United States Patent [19]

Tayler

[11] Patent Number: 5,244,866
[45] Date of Patent: Sep. 14, 1993

[54] METHOD OF INHIBITING SPROUT GROWTH ON AGRONOMIC CROPS USING ACETOHYDROXY ACID SYNTHASE INHIBITING HERBICIDES

[75] Inventor: Peter N. Tayler, Hampshire, England

[73] Assignee: American Cyanamid Company, Stamford, Conn.

[21] Appl. No.: 923,392

[22] Filed: Jul. 31, 1992

[51] Int. Cl.$^5$ ............................................. A01N 43/52
[52] U.S. Cl. .................................... 504/253; 504/276; 504/118
[58] Field of Search ...................... 71/92, 65; 504/253, 504/276

[56] References Cited

U.S. PATENT DOCUMENTS 4,957,536  9/1990  Orwick et al. ........................... 71/92

FOREIGN PATENT DOCUMENTS 0072347  7/1983  European Pat. Off. .

Primary Examiner—Richard L. Raymond
Assistant Examiner—B. Bembenick
Attorney, Agent, or Firm—Michael P. Morris

[57] ABSTRACT

This invention relates to the use of acetohydroxyacid synthase (AHAS) inhibiting herbicides to prevent or delay sprout formation in agronomic crops. More particularly, this invention relates to the application of imidazolinones on tubers, such as potatoes, to inhibit the post-harvest growth of sprouts.

15 Claims, No Drawings

METHOD OF INHIBITING SPROUT GROWTH ON AGRONOMIC CROPS USING ACETOHYDROXY ACID SYNTHASE INHIBITING HERBICIDES

This invention relates to the use of acetohydroxyacid synthase (AHAS) inhibiting herbicides to prevent or delay sprout formation in agronomic crops. More particularly, this invention relates to the application of imidazolinones on tubers, such as potatoes, to inhibit the post-harvest growth of sprouts.

BACKGROUND OF THE INVENTION

Among agronomic crops, fleshy roots and stems, such as tubers and bulbs, have become an important food source. Tubers, such as potatoes, carrots, beets, radishes and turnips, and bulbs, such as onions, should be eaten within a few months of harvest. Otherwise, sprouts may form, signaling a decrease in quality of the the crop. For example, the eyes of a potato are nodes where bud sprouts may grow leading to a decrease in starch content of the potato, making it less commercially desirable. In addition, once harvested, the tuber (or bulb) may lose weight through respiration and transpiration and may become blemished, dessicated and rotted.

Thus, an important consideration for distribution and sale of agronomic crops is the total time from harvest to ultimate consumer use. Unfortunately, crops are often stored for long periods of time prior to their ultimate use. Efforts have been made to minimize this time period and to extend the useful life of the crop such that it retains its utility and commercial appeal. Such efforts generally are directed to controlling ambient conditions such as ventilation, temperature, humidity, and light.

Chemicals have also been used to improve the storage life of agronomic crops. For example, tecnazene (Fusarex ®), and CIPC or chloropham (Mirvale ®) have been used for tuber sprout suppression. However, both of these products have problems.

Tecnazene, a fungicide, has been found to be toxic to fish downstream of processing plants. Residues have also been detected in soil and drinking water. In fact, a six week treatment withholding period has been set for making potatoes treated with tecnazene available for distribution. The unacceptably high toxicity and cost of tecnazene, and the increasing use of fungicides such as imazalil and TBZ to seed potatoes, have contributed to the decreasing use of tecnazene.

CIPC is an old and inexpensive product. The need to apply CIPC as a vapor, however, results in an uneven distribution when applied to crops in storage. Such uneven distribution leads to excessive, and potentially harmful residues. In addition, CIPC must be applied several times during the storage period leading to an increase in such residues. A three week treatment withholding period has been set for CIPC. Other chemicals, such as maleic hydrazide and various alkyl napththalenes, (e.g., DIPN) have also been used to inhibit sprout formation on such crops with little success.

Thus, there remains a need for an effective, low cost, environmentally friendly sprout suppressant.

It is therefore an object of this invention to provide a method of using herbicides to inhibit the growth of sprouts on tubers and bulbs.

It is further an object of this invention to provide a post-harvest sprout inhibiting treatment for tubers and bulbs which is easily and uniformly applied in a single treatment.

It is yet another object of this invention to provide a sprout inhibiting treatment which has low toxicity and a reduced treatment withholding period.

These and other objects of the invention will become apparent from the detailed description of the invention which follows.

SUMMARY OF THE INVENTION

This invention relates to the use of AHAS inhibiting herbicides to prevent or delay sprout formation in agronomic crops. More particularly, this invention relates to the application of imidazolinones on tubers, such as potatoes, to inhibit the post-harvest growth of sprouts.

DETAILED DESCRIPTION OF THE INVENTION

Imidazolinones are part of a class of herbicides that inhibit acetohydroxyacid synthase (AHAS), the enzyme responsible for the synthesis essential of amino acids in plants. See, e.g., U.S. Pat. No. 4,761,373. Such AHAS inhibiting herbicides have been shown to produce growth regulating biological effects on agronomic crops (see, e.g., W. A. Kleschick et al., "New Herbicide Derivatives of 1,2,4-Triazolo[1,5-a]pyrimidine", *Pestic. Sci.*, 29, pages 341–355 (1990)). For example, U.S. Pat. No. 4,957,536 refers to the use of imidazolinones to increase axillary branching, tillering, flowering and yield of growing agronomic and horticultural crops. Surprisingly, we have found that certain AHAS inhibiting herbicides, in particular imidazolinones, are unexpectedly effective in inhibiting sprout formation in tubers and bulbs. As used herein, agronomic crops include, for example, bulbs, such as onions, and tubers, such as carrots, turnips, beets, radishes and especially, potatoes.

This invention, for the first time, provides a safe and effective treatment for inhibiting sprout formation on fleshy roots and stems, such as tubers or bulbs, preferably while in storage. The treatment comprises the application of an effective sprout inhibiting amount of an AHAS inhibiting herbicide, for example, sulfonylureas, sulfamoylureas (sulfonamides), triazolopyrimidines and especially, imidazolinones, or combinations thereof, to agronomic crops before, or preferably after harvest. Preferred AHAS inhibiting herbicides in accordance with this invention are imidazolinones, such as those described in U.S. Pat. No. 4,798,619 which is incorporated herein by reference. More preferred are imazapyr (Arsenal ®; American Cyanamid Co.) and imazethapyr (Pursuit ®; American Cyanamid Co.). Most preferred is imazethapyr.

Such herbicides may be applied to tubers or bulbs before or after harvest, as a tank mix, as a spray, as an aerosol, in a dip, or by other methods known in the art. Such herbicides are preferably applied as a spray, alone, or in conjunction with an effective sprout formation inhibiting amount of other herbicidally and/or fungicidally active compounds. The sprout inhibiting effect of such compositions is greatest when applied shortly after harvest.

These AHAS inhibiting herbicides are effective to inhibit sprout growth when administered at between about 0.05 g and 1 g per ton of agronomic crop, preferably between about 0.25 and 1 g, most preferably at about 0.5 g per ton. These herbicides are typically diluted, preferably in an aqueous solution when their water soluble ammonium salt forming cation is used, prior to application to the crop, as a dilute aqueous spray. When mixed in aqueous solution, the herbicide dose is generally between about 50 ppm and 1000 ppm, i.e., between about 0.05 g and 1 g per liter of aqueous solution per ton of crop. Higher doses of AHAS inhibiting herbicides, however, may be used for certain agronomic crop according to the particular application without departing from the scope of this invention. For example, up to about 5000 ppm or more may be used, depending on the particular crop, particular treatment combination, and the ambient conditions.

The resulting solution may also include up to about 1% by volume of a nonionic surfactant, preferably about 0.25% by volume. Preferred surfactants include Agral, BIOFILM ® (a product of Colloidal Products Corp.) which is a mixture of alkylarlypolyoxyethanol, free and combined fatty acids, glycol ethers, dialkylbenzene carboxylate and 2-propanol; multifilm X-77 (Ortho); Igepal DM-710 (GAF Corporation) which is an alkylphenoxypoly (ethyleneoxy) ethanol; and other typical surfactants such as Tween ® and the like.

The amount of herbicide, or combination of herbicides, effective as a sprout suppressant will vary somewhat according to the particular herbicide(s), the type and the amount of the crop, the duration of storage and the size and configuration of the storage container, the environment in which the treatment is administered, and the like. As described above, about 50 ppm-1000 ppm in an aqueous solution is effective for most applications. Application of the herbicidal compositions at such rates is not only effective at inhibiting sprout formation but shows reduced toxicity compared to other fumigant sprout suppressants, particularly when imdiazolinones are used. Another advantage of these compositions is that they are stable for long periods of time at room temperature.

The herbicidal compositions may also be formulated as emulsifiable concentrates, flowable liquid concentrates, or wettable powders which are diluted with water, other suitable polar solvent or oil carrier, generally in situ, and then applied as a dilute spray. Said compositions may also be formulated in suspension concentrates, microemulsions, and the like, all of which lend themselves to plant (foliage), root, stem, seed, tuber, or bulb applications to provide the requisite sprout suppression. Such formulations include herbicides admixed with inert, solid or liquid diluents.

For example, wettable powders, dusts and dust concentrate formulations can be prepared by grinding and blending together about 25% to about 85% by weight of formula I compounds and about 75% to about 15% by weight of a solid diluent such as bentonite, diatomaceous earth, kaolin, attapulgite, or the like, about 1% to 5% by weight of a dispersing agent such as sodium lignosulfonate, and about 1% to 5% by weight of a nonionic surfactant, such as octylphenoxy polyethoxy ethanol, nonylphenoxy polyethoxy ethanol, or the like.

A typical flowable liquid concentrate can be prepared by admixing about 40% by weight of the active ingredient with about 2% by weight of a gelling agent such as bentonite, about 3% by weight of a dispersing agent such as sodium lignosulfonate, about 1% by weight of a thickener such as polyethylene glycol, and water.

A typical emulsifiable concentrate can be prepared by dissolving about 5% to 50% by weight of the active ingredient in about 95% to 50% by weight of a solvent such as N-methylpyrrolidone, isophorone, toluene, butyl cellosolve, methyl acetate, propylene glycol monomethyl ether, or the like, and dispersing therein about 1% to 5% by weight of a nonionic surfactant such as an alkylphenoxy polyethoxy alcohol.

The compositions of the invention are prepared for use by adding a predetermined quantity of formulated product, such as described above, to the desired volume of water, other suitable solvent or liquid or solid carrier, alone or in combination with one or more other agronomic chemicals for sequential or simultaneous use. Advantageously, the compounds of the invention may be used effectively in conjunction with, or in combination with, other biological chemicals including, but not limited to, biologically effective amounts of anilazine, benalaxyl, benomyl, bitertanol, bordeaux mixture, carbendazim, carboxin, capatafol, captan, chlorothalonil, cyproconazole, dichloran, diethofencarb, diniconazole, dithianon, dodine, edifenphos, fenarimol, fenbuconazole, fenfuram, fenpropidin, fenpropimorph, fentin hydroxide, ferbam, flusilazole, flusulfamide, flutriafol, folpet, fosetyl, fuberidazole, guazatine, hexaconazole, imazalil, iprobenfos, iprodione, mancozeb, maneb, metalaxyl, metiram, myclobutanil, nuarimol, ofurace, oxadixyl, oxycarboxin, penconazole, probenazole, prochloraz, propiconazole, pyrazophos, tebuconazole, thiabendazole, thiophanate, thiophanate-methyl, triadimefon, triadimenol, triarimol, tricyclazole, tridemorph, triflumizole, triforine, vinclozolin, zineb, and the like.

Where compositions of the invention are to be employed in combination treatments with other pesticidal or fungicidal agents, the composition may be applied as an admixture of the components as described hereinabove or may be applied sequentially.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1-5

Five imidazolinone treatment groups of ten potatoes each were evaluated. Sprout development was assessed at about 8 weeks and 18 weeks post treatment. Potatoes from each treatment group were dipped for one minute each, respectively, in an aqueous solution containing 50 ppm, 100 ppm, 250 ppm or 500 ppm of Assert ® (imazamethabenz-methyl), Scepter ® (imazaquin), Cadre ® (imazamethapyr), Pursuit ® (imazethapyr) or Arsenal ® (imazapyr). The solutions also contained 0.25% multifilm X-77 as a surfactant to enhance wetting. Potatoes from the positive control treatment groups were sprayed three times in storage at approximately 4, 10 and 16 weeks into the 18 week test period with either 10 ppm or 20 ppm of the standard material (CIPC), and the last group (control) received no treatment. All potatoes were allowed to dry for one hour, rotated once during that time. All potatoes were then kept in the dark, at room temperature, for the duration of the treatment period. After the treatment period was over, the number of sprouts were counted and their fresh weight taken. The results indicating the number of potatoes having sprouts measuring at least $\frac{1}{4}''$ and fresh weight (g) per group are presented below in Tables 1-5.

TABLE 1

Effect of imazethapyr treatments on sprouting of potatoes

| Treatment ppm | | # of sprouts >5 mm in length mean (of 10 potatoes per treatment) | Total Fresh wt of sprouts-g | % inhibition of fresh wt |
|---|---|---|---|---|
| Untreated Control | | 73 | 19.2 | — |
| imazethapyr | 50 | 36 | 13.1 | 32 |
| | 100 | 29 | 3.0 | 58 |
| | 250 | 13 | 4.3 | 78 |
| | 500 | 12 | 3.3 | 83 |

TABLE 2

Effect of imazaquin treatments on sprouting of potatoes

| Treatment ppm | | # of sprouts >5 mm in length mean (of 10 potatoes per treatment) | Total Fresh wt of sprouts-g | % inhibition of fresh wt |
|---|---|---|---|---|
| Untreated Control | | 85 | 16.5 | — |
| imazaquin | 50 | 65 | 16.3 | 1 |
| | 100 | 64 | 18.0 | — |
| | 250 | 65 | 16.9 | — |
| | 500 | 59 | 14.3 | 13 |

TABLE 3

Effect of imazamethapyr treatments on sprouting of potatoes

| Treatment ppm | | # of sprouts >5 mm in length mean (of 10 potatoes per treatment) | Total Fresh wt of sprouts-g | % inhibition of fresh wt |
|---|---|---|---|---|
| Untreated Control | | 91 | 11.9 | — |
| imazamethapyr | 50 | 68 | 11.6 | — |
| | 100 | 68 | 14.2 | — |
| | 250 | 73 | 13.9 | — |
| | 500 | 19 | 3.1 | 74 |

TABLE 4

Effect of imazapyr treatments on sprouting of potatoes

| Treatment ppm | | # of sprouts >5 mm in length mean (of 10 potatoes per treatment) | Total Fresh wt of sprouts-g | % inhibition of fresh wt |
|---|---|---|---|---|
| Untreated Control | | 63 | 21.5 | — |
| imazapyr | 50 | 54 | 20.1 | 7 |
| | 100 | 57 | 20.3 | 6 |
| | 250 | 46 | 21.1 | — |
| | 500 | 45 | 17.9 | 17 |

TABLE 5

Effect of imazamethabenz-methyl treatments on sprouting of potatoes

| Treatment ppm | | # of sprouts >5 mm in length mean (of 10 potatoes per treatment) | Total Fresh wt of sprouts-g | % inhibition of fresh wt |
|---|---|---|---|---|
| Untreated Control | | 46 | 16.4 | — |
| imazametha-benz-methyl | 50 | 12 | 2.0 | 88 |
| | 100 | 0 potatoes | 0 | 100 |
| | 250 | 0 rotted in | 0 | 100 |
| | 500 | 0 storage | 0 | 100 |

EXAMPLES 6-7

Examples 6 and 7 compare the effectiveness of a 1000 ppm dose of imazethapyr and imazapyr to CIPC for suppression of potato sprouts. Four major varieties of potato, having varying dormancy periods, were tested. The potatoes were treated once with varying doses of Pursuit ® (imazethapyr) or Arsenal ® (imazapyr) before storage. The CIPC was applied at its usual dose (10-20 ppm) once as a dip (Example 6), and three times in storage as a spray mist (Example 7).

TABLE 6

Effect of imazethapyr and imazapyr on sprouting of potatoes

| Treatment-ppm* | | # of sprouts >5 mm in length (mean of 10 potatoes per treatment) | % of sprouts >5 mm in length |
|---|---|---|---|
| Untreated Control | | 54 | 97 |
| Standard material (CIPC) | 10 | 51 | 98 |
| | 20 | 48 | 98 |
| imazethapyr | 50 | 33 | 75 |
| | 100 | 33 | 64 |
| | 250 | 7 | 13 |
| | 500 | 11 | 21 |
| | 1000 | 6 | 12 |
| imazapyr | 50 | 38 | 72 |
| | 100 | 34 | 63 |
| | 250 | 10 | 15 |
| | 500 | 4 | 8 |
| | 1000 | 11 | 17 |

*Treatments were applied by submerging potatoes for 2 minutes in the appropriate solution.

TABLE 7

Effect of imazethapyr treatments on sprouting of potatoes Sprouting Indices*

| | Potato Variety | | | | | | | |
|---|---|---|---|---|---|---|---|---|
| | Maris Piper | | Pentland Dell | | Record | | Romano | |
| Treatment | 1** | 2** | 1 | 2 | 1 | 2 | 1 | 2 |
| Untreated control | 10.8 | 17.5 | 5.7 | 20.3 | 7.6 | 22.1 | 1.1 | 10.1 |
| CIPC | 3.3 | 2.4 | 2.8 | 2.8 | 6.2 | 7.2 | 0.05 | 1.5 |
| imazethapyr 250 ppm | 2.1 | 2.1 | 1.8 | 3.0 | 3.1 | 6.6 | 1.0 | 4.1 |
| imazethapyr 500 ppm | 1.8 | 2.0 | 1.5 | 2.2 | 2.7 | 4.5 | 1.2 | 2.0 |
| imazethapyr 1000 ppm | 1.8 | 1.5 | 1.6 | 1.9 | 2.2 | 3.6 | 0.8 | 1.9 |

*Measurement taken on a total of 60 potatoes per variety, per treatment at each assessment date. Values reflect the mean of the sprout growth histogram distribution: 0(0); 0-3 mm (1.5); 3-10 mm (6.5); 10-20 mm (15) and >20 (actual measurement, multiplied by the number of potatoes having sprouts in that size category.
**1 refers to 1st assessment (8 weeks); 2 refers to 2nd assessment (18 weeks).

As demonstrated in the Tables, good sprout suppression was observed with the imidazolinones, particularly imazethapyr and imazapyr. Except for Romano, which has a long dormancy period, one treatment of imazethapyr at 250 ppm was as good as or better than three applications of the standard material.

I claim:
1. A method for inhibiting sprout formation on tubers comprising administering to said tubers an effective sprout inhibiting amount of an imidazolinone.
2. The method according to claim 1 wherein the imidazolinone is administered to the tuber post-harvest.
3. The method according to claim 1 wherein the imidazolinone is selected from imazethapyr and imazapyr.
4. The method according to claim 3 wherein the imidazolinone is imazethapyr.
5. The method according to claim 1 in combination with a biologically effective amount of one or more other agronomic chemicals.

6. The method according to claim 1 wherein the tuber is selected from potatoes, carrots, beets, radishes and turnips.

7. The method according to claim 6 wherein the tuber is a potato.

8. The method according to claim 1 wherein the imidazolinone is administered as a tank mix, as a spray, as an aerosol or in a dip.

9. The method according to claim 8 wherein the imidazolinone is administered as a spray.

10. The method according to claim 2 wherein the effective sprout inhibiting amount comprises between about 0.05 g and 1 g per ton of tubers.

11. The method according to claim 10 wherein the effective sprout inhibiting amount comprises between about 0.25 g and 1 g per ton of tubers.

12. The method according to claim 11 wherein the effective sprout inhibiting amount comprises about 0.5 g per ton of tubers.

13. The method according to claim 10 wherein said amount of imidazolinone is mixed with about one liter of an aqueous solution.

14. The method according to claim 13 wherein the aqueous solution further comprises up to about 1% by volume of a nonionic surfactant.

15. The method according to claim 14 wherein the nonionic surfactant is selected from Agral, BIOFILM ®, multifilm X-77 and Igepal DM-710.

* * * * *